United States Patent
Bachand et al.

(10) Patent No.: US 6,489,172 B1
(45) Date of Patent: *Dec. 3, 2002

(54) SALIVA SAMPLING DEVICE

(75) Inventors: Steven S. Bachand, Laguna Niguel, CA (US); Lee Huu Nguyen, Irvine, CA (US); Geoffrey R. Anderson, Lakewood, CA (US)

(73) Assignee: Varian, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,875

(22) Filed: Jan. 5, 2000

(51) Int. Cl.$^7$ .................................................. G01N 1/10
(52) U.S. Cl. .................... 436/180; 422/58; 422/102; 600/572; 600/573
(58) Field of Search ............... 422/55, 56, 58, 422/61, 99, 100, 101, 102; 436/174, 180, 518; 600/572, 573, 575, 580; 604/1, 2, 111; 206/569

(56) References Cited

U.S. PATENT DOCUMENTS

| | | | |
|---|---|---|---|
| 4,014,322 A | * | 3/1977 | Shah |
| 4,418,702 A | | 12/1983 | Brown et al. |
| 4,580,577 A | * | 4/1986 | O'Brien et al. ............. 422/101 |
| 4,834,706 A | * | 5/1989 | Beck et al. ................. 604/111 |
| 5,103,836 A | | 4/1992 | Goldstein et al. |
| 5,260,031 A | | 11/1993 | Seymour ................... 422/101 |
| 5,268,148 A | * | 12/1993 | Seymour ................... 422/101 |
| 5,335,673 A | | 8/1994 | Goldstein et al. |
| 5,376,337 A | | 12/1994 | Seymour |
| 5,393,496 A | | 2/1995 | Seymour |
| 5,494,646 A | | 2/1996 | Seymour |
| 5,609,160 A | | 3/1997 | Bahl et al. |
| 5,647,859 A | * | 7/1997 | Kalin ......................... 604/111 |
| 5,766,962 A | * | 6/1998 | Childs et al. ............... 436/518 |
| 5,830,410 A | * | 11/1998 | Thieme et al. ............... 422/58 |
| 5,910,122 A | | 6/1999 | D'Angelo |
| 5,922,614 A | | 7/1999 | Cesarczyk .................. 436/180 |
| 5,968,746 A | | 10/1999 | Schneider |
| 5,981,293 A | | 11/1999 | Charlton |
| 6,176,836 B1 | | 1/2001 | Trudil et al. |
| 6,277,646 B1 | * | 8/2001 | Guirguis et al. ............ 436/174 |

* cited by examiner

Primary Examiner—Joseph W. Drodge
(74) Attorney, Agent, or Firm—Walter A. Hackler

(57) ABSTRACT

A saliva sampling device includes an expresser cup, an absorbent foam swab capable of absorbing a fluid specimen, and a flexible tether affixed to the foam swab. The foam swab is used to collect a sample of a fluid specimen such as saliva, and the tether is adapted to enable a user to sanitarily draw the saturated foam swab into the expresser cup in which the foam swab becomes compressed; and the absorbed fluid is expressed therefrom in a drop by drop fashion. The device also may include a platform having a reagent strip for absorbing the expressed fluid to reveal test results. The device may also include a divider for separating the expressed fluid into two or more aliquots prior to the testing thereof such that one of the aliquots may be used for confirmation or later testing of the fluid. In one embodiment, the expresser cup includes a conical cross section to effect gradual compression of the foam swab.

35 Claims, 2 Drawing Sheets

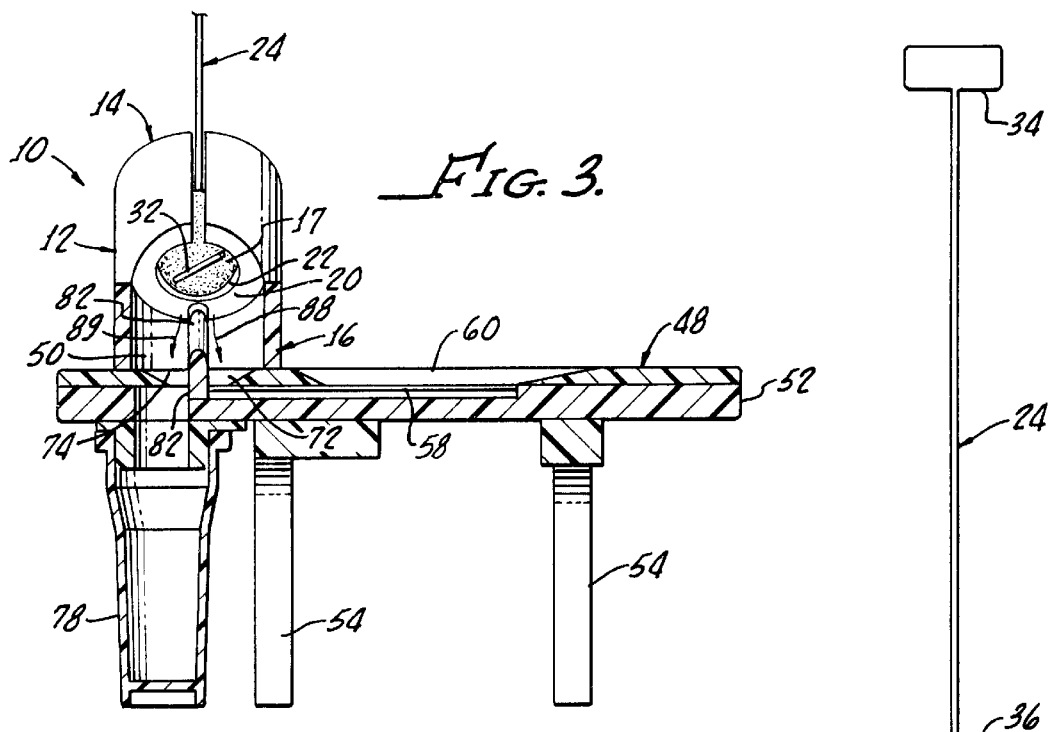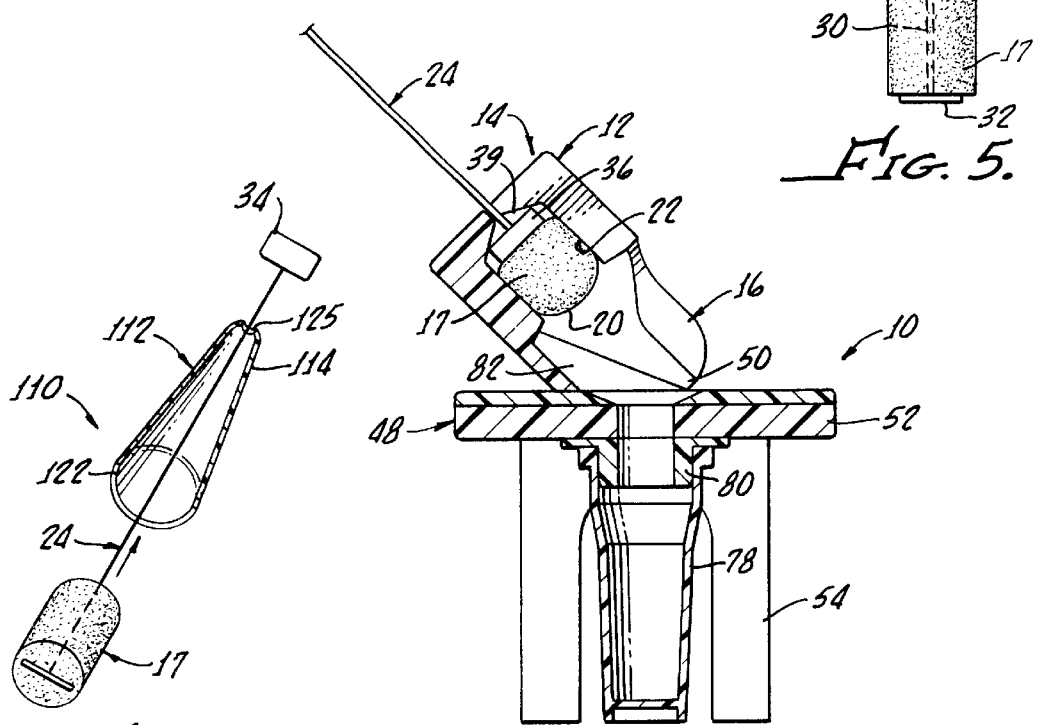

SALIVA SAMPLING DEVICE

The present invention generally relates to fluid specimen collection devices, and more specifically relates to a saliva sampling device and method for extracting saliva for use in diagnostic tests.

Unlike other forms of fluid specimens such as blood or urine, collection of oral fluid, such as saliva, for diagnostic purposes is complicated by many factors, for example, the low volumes of salivary fluid secreted, the relatively high viscosity of the fluid, and the diverse anatomic dispersion of the salivary glands. These problems become compounded when a single saliva sample is to be divided into two or more portions as is sometimes desired. Most techniques for collection involve the use of capillary tubes, suction into micro pipettes, chewing on paraffin, and/or aspiration from the mouth into polypropylene syringes.

In addition, testing of salivary specimens has not yet been extensively developed. Blood and urine samples have for long been the primary fluids used for testing for disease as well as for evidence of substance abuse. However, it is now known that human saliva carries lymphocytes, plasma cells and immunoglobulins that are directly related to the immunoglobulins found in the blood. In addition, saliva carries immunoglobins that are believed to be peculiar to saliva, for example, the antibody known as secretory IgA. Because of the association between immunoglobulins of the blood and saliva, as well as the occurrence of secretory IgA, antigen-antibody tests have been conducted on salivary fluid to assess the value of such tests as screening tools for disease.

U.S. Pat. No. 5,922,614 to Cesarczyk describes a Sample Collection Method with Extraction Sleeve. The device is designed for collecting saliva or urine samples using an absorbent, elongate foam member secured within a hollow tube and having a portion extending therefrom. The foam member is used to absorb a fluid specimen. The foam member and hollow tube are slidably mounted within an outer sleeve covering the foam member. Fluid is collected by a user exerting pressure against the sleeve to compress the foam member and thereby release the fluid. According to Cesarczyk, the device provides an aseptic, easy to use device for collecting a fluid sample such as saliva.

The present invention exemplifies an improved oral fluid collection device which is easier to use than other devices in the field that are those presently available.

The present invention provides an improved sampling device for collecting and delivering an oral fluid specimen such as saliva, for diagnostic testing.

SUMMARY OF THE INVENTION

Accordingly, a method and device are provided for both collecting and delivering a fluid sample, such as blood, urine or saliva for diagnostic testing. It is noted that the device is especially advantageous for samples of which only a low volume of sample is available for collection, specifically saliva.

The device generally comprises an expresser, having a distal open end connected to a port, and a generally closed proximal end. The expresser is adapted to receive an absorbent member substantially saturated with a fluid specimen, through the distal opening. As the absorbent member is pulled through the distal opening and into the port, the port provides means for compressing the absorbent member to effect expression of the fluid specimen therefrom the absorbent member.

Connected to the expresser distal open end is a platform for collecting at least a portion of the specimen as it is expressed from the absorbent member. The platform preferably is adapted to provide means for testing the fluid specimen. For example, the platform may include a sample well for receiving drops of expressed fluid. To facilitate flow of the expressed fluid into the sample well, the expresser may be disposed at an angle with respect to the generally horizontal platform.

The sample well may include a first port and a second port, comprising, for example a test port and a confirmation port respectively. In addition, the platform may include a lateral flow test strip in fluid communication with the test port, and a confirmation container in fluid communication with the confirmation port. Preferably, the platform has a closed top surface encasing the test strip, and a viewing window exposing a portion of the strip.

In one especially advantageous embodiment, the device further comprises means for dividing the fluid expressed from the expresser. For example, a partition, disposed between the test and confirmation ports and extending at least partially into the expresser container is provided. A ratio of confirmation sample to lateral flow sample could be adjusted by changing location and/or configuration of the dividing partition.

In one embodiment of the invention, an absorbent member is provided, as well as tether means for enabling manual handling of the absorbent member. The expresser distal opening may include an inlet, sized for passage of the absorbent member, and a longitudinal slot in communication with the inlet, sized for passage of the tether means. By controlling the pulling of the tether, the user may cleanly and controllably express the fluid, drop by drop, to be used for testing/diagnostic purposes.

BRIEF DESCRIPTION OF THE DRAWINGS

The objects and advantages of the present invention: will be more clearly understood and appreciated with reference to the following detailed description when considered in conjunction with the appended drawings of which:

FIG. 3 shows a cross sectional view of the device taken along line 3—3 of FIG. 2;

FIG. 4 shows a cross sectional view of the device taken along line 4—4 of FIG. 2;

FIG. 5 shows a side view of an absorbent member and tether combination suitable for use in the device shown in FIGS. 1–4;

FIG. 7 shows an expresser cup useful with a method of the present invention.

DETAILED DESCRIPTION

Figure 1:
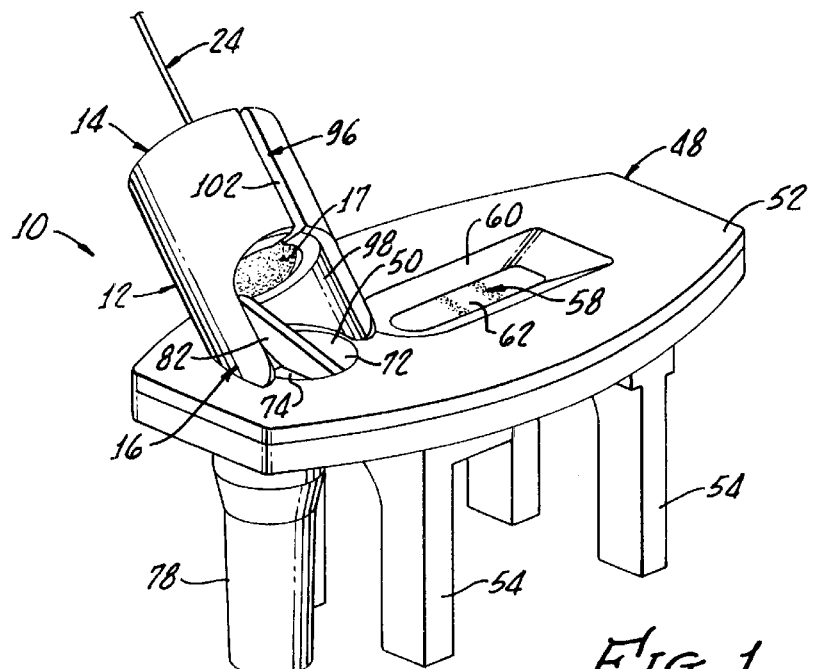
FIG. 1 shows a perspective view of a saliva sampling device in accordance with the present invention, including an expresser adapted to receive an absorbent member, the expresser including a port adapted to compress the absorbent member to effect expression of saliva fluid absorbed by the absorbent member, and collection means, comprising a platform connected to the expresser, for collecting the portion of fluid for testing.

Turning now to FIGS. 1–4, an embodiment of the fluid specimen sampling device 10 in accordance with the invention is shown. The device 10 generally comprises a substantially cylindrical member, hereinafter referred to as an "expresser" 12 for reasons which will later become apparent. The expresser 12 includes a proximal, generally closed end 14 and a distal, substantially open end 16. The expresser 12 is adapted to receive an absorbent member 17 (not in view in FIG. 2) through the distal open end 16, said absorbent member 17 to be described in greater detail hereinafter. In accordance with a method of the present invention, a fluid specimen or sample is applied to the absorbent member 17 and is expressed therefrom for collection and testing. For example, the absorbent member 17 may comprise an absorbent sponge, foam swab or like material capable of absorbing a fluid specimen such as saliva, sized to be comfortably placed in a mouth of a patient or subject person (not shown). After the foam swab 17 is so placed in the mouth, it is allowed to remain in the mouth for a sufficient time to allow a sample of saliva fluid to be absorbed thereby. The time for absorption of a sufficient amount of specimen will generally vary depending upon the particular subject person.

The expresser 12 is designed to enable sanitary, effective expression of at least a portion of the fluid sample that has been absorbed by the foam swab 17 in an amount sufficient for testing and/or collection. Referring now to FIGS. 3 and 4, the expresser 12 includes a port 20, defined by inner walls 22 thereof, the port terminating at the proximal end 14. The expresser port 20 provides means for compressing the foam swab 17 as the foam swab 17 is passed into the expresser 12. A tether 24, connected to the absorbent member 17 is provided for enabling a user to pull the absorbent member 17 into the port 20.

As shown in FIGS. 3 and 5 the tether 24 may comprise a flexible, plastic monofilament having a distal portion 30 passing through the absorbent member 17 with a hook 32 outside of the absorbent member 17, thereby providing a simple, yet secure engagement therebetween. A handle 34 (shown only in FIG. 5) is provided for facilitating manual handling of the foam swab 17.

Referring back now to FIGS. 1–3, the device 10 further comprises means for collecting the expressed fluid sample. Specifically, for example, a platform 48 having a sample well 50 in communication with the expresser distal opening 16 may be provided wherein the platform 48 includes a plastic housing 52 supported by legs 54, skirt (not shown) or other suitable structure. The housing 52 is structured to accommodate at least one reagent strip or one lateral flow test strip 58 made of nitrocellulose or other suitable material, said lateral flow test strip 58 having a portion 60 being exposed to the sample well 50. Reagent strip 58 will not be further described in detail herein, as lateral flow test strips suitable for use with the present invention are well known in the art of diagnostic testing devices.

Preferably, as shown most clearly in FIGS. 1 and 4, in order to effectively channel the flow of expressed fluid into the sample well 50, the expresser 12 is connected to the platform 48 at an inclined angle, for example, of about 45 degrees.

Upon deposit of the expressed sample fluid into the sample well 50, the fluid begins migration along the test strip 58. A window 60 in the platform 48 provides means for enabling viewing of a test strip portion 62 that reveals validity, positive/negative or quantitative test results.

In one especially advantageous aspect of the invention, the sample well 50 may be divided into two or more sub-ports, for example, a first port 72 and a second port 74. The first port 72 and second port 74 will be hereinafter designated as a test port and a confirmation port, respectively, although it is contemplated that the ports may both function as different test ports, for example. As shown in FIG. 3, the test port 72 is in fluid communication with the lateral flow test strip 58 such that a first portion of the fluid, deposited in the test port 72, will immediately begin migration along the strip 58. Similarly, the confirmation port 74 may be in fluid communication with a confirmation container 78 for collecting and/or storing a second portion of the fluid for confirmation of patient identity, test validity or other processing steps to be performed at a later time.

Figure 6:
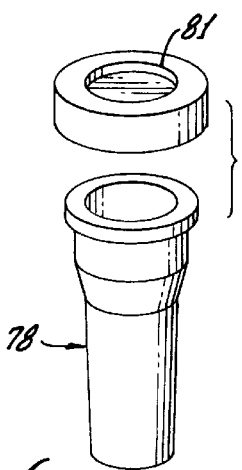
FIG. 6 shows a confirmation container useful in the device of the present invention for storing a portion of the expressed saliva fluid for processing at a later time.

Referring to FIGS. 1, 3 and 4, the confirmation container 78 is shown depending from the platform 48 immediately beneath the confirmation port 74. Preferably, as shown in FIG. 4, suitable means, for example cooperating plug 80 depending from the platform, is provided for removably coupling the container 78 to the platform 48. Turning to FIG. 6, additionally provided is a tamper evident closure cap 81 for sealing the confirmation container 78 after it has been removed from the platform 48.

Turning again to FIGS. 1–4, means for dividing the sample fluid is provided. More specifically, a partition 82, extending substantially normal to the platform 48 and at least partially into the expresser 12 is provided for dividing the fluid sample into two or more portions as the fluid is being expressed and collected. The partition 82 is secured to the platform 48 within the sample well 50 and may be substantially flush with the inner wall 22 defining the expresser port 20 (see FIGS. 3 and 4). As shown in FIG. 3, the partition 82 functions to direct a portion of the expressed fluid into the test port 72 (flow portion represented by arrow 88) and another portion of the expressed fluid into the confirmation port 74 (flow represented by arrow 89). This feature of the invention enables a user to divide and perform multiple tests or procedures on an individual sample of a fluid, such as saliva which is typically difficult to collect in any substantial quantity.

It is contemplated that an alternative feature of the invention includes manually squeezable walls of the expresser 12, provided as an alternative or additional means for expressing fluid from the foam swab 17. More specifically, after the absorbent member 17 is pulled into the expresser 12, drops of the fluid may be extracted therefrom by the user manually applying pressure to, or squeezing, the expresser 12. A suitable material for the squeezable expresser is a low density polyethylene plastic.

Figure 2:
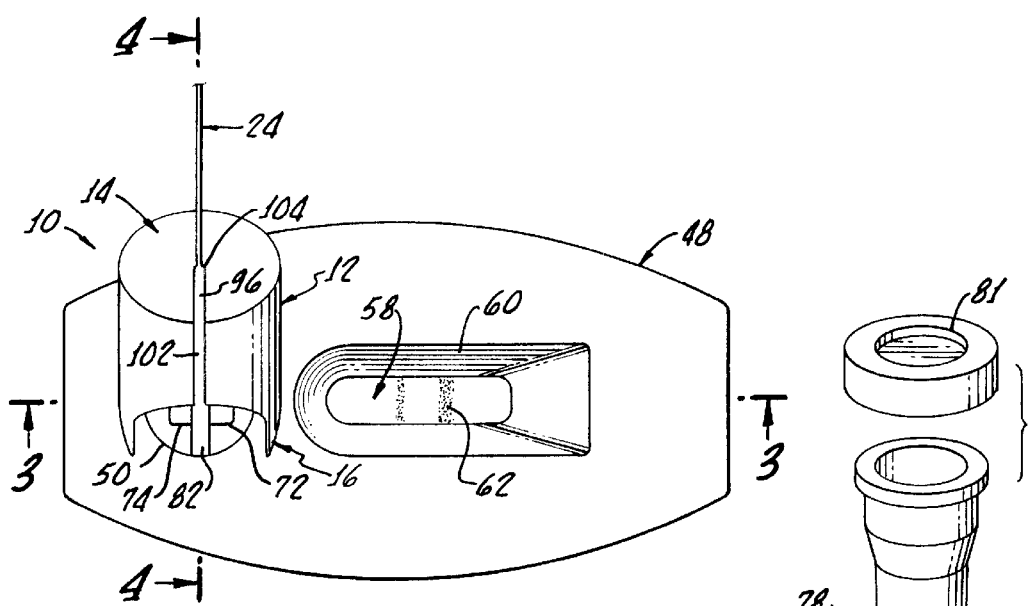
FIG. 2 shows a top view of the device in FIG. 1.

Referring back now to FIGS. 1 and 2, the device 10 may further comprise means 96 for facilitating insertion of the absorbent member 17 and tether 24 into the expresser 12. Particularly, the expresser 12 may include a wide inlet 98 sized for substantially uncompressed passage of the absorbent member 17, and a longitudinal slot 102 in communication with the distal end inlet, sized for passage of the tether 24. As shown in FIG. 2, the slot 102 extends from the wide inlet 98 through the proximal end 14 of the expresser 12.

The device 10 may further include means for holding the absorbent member 17 in a compressed position to enable a user to manually release the tether after the absorbent member 17 has been compressed without causing the absorbent member 17 to expand and potentially reabsorb the expressed fluid. The user may therefor attend to other tasks while waiting for the absorbed fluid to be expressed from the foam swab 17 and flow along the expresser inner walls 22. It noted that this feature is especially advantageous for use with high viscosity, cohesive fluids such as saliva which tend to flow relatively slowly.

Collecting and testing of a fluid specimen may be performed as follows. The absorbent foam 17, having the tether 24 secured thereto, is placed in the mouth of a patient, or subject person, and the foam 17 is kept in the mouth until it is substantially saturated with saliva fluid. A technician, or other user of the device 10 can thereafter sanitarily handle the absorbent member 17 by means of the handle 34. The technician places the saturated foam 17 into the wide inlet portion 98 of the slot means 96 and the tether 24 is gently pulled toward and into the slot 102 such that it eventually projects from the expresser 12 through the proximal end 14 thereof.

To express the absorbed fluid from the foam 17, the technician gently pulls the tether handle 34 to cause the foam 17 to enter the port 20 and become compressed thereby and eventually be squeezed within the expresser port 20.

A small disk 36, or the like, made for example of rubber or plastic, may be slidably engaged to the tether 24 such that the fluid specimen will be substantially prevented from leaking from the expresser 12 during the compression of the swab.

Expressed fluid is channeled toward the sample well 50 and divided by the partition 82. Means, such as a narrow end 104 of the slot 102, may be provided for locking the tether 24, thereby holding the foam 17 in a compressed position, such that the expressed fluid will not inadvertently be reabsorbed by the foam swab 17. A portion of the fluid is collected in the confirmation container 78 which is may then removed from the platform and sealed with cap 81. The technician may read test results through window 60.

Preferably, the device is configured on such a way that the reagent strip may be successfully photocopied or scanned to preserve a copy of the test results. For example the device 10 may structured such that the expresser is easily removable from the platform lowering the profile of the test device 10.

Turning now to FIG. 7, the alternative saliva sampling device 110, comprising conical expresser 112, hereinafter referred to as "expresser cup" 112, is shown, with like parts being represented by like reference numerals. This device 110 is useful for collecting and testing an oral fluid sample, in accordance with a method the invention, and may be used independently and exclusively of the platform 48. For example, the device 110 may be used to provide a particular number of drops of an absorbed fluid sample, to be deposited onto conventional fluid specimen testing apparatus or into collection canisters (not shown).

In this embodiment, the tether foam 17 is threaded through the expresser cup 112, without the expresser cup 112 being secured to the platform 48 of FIGS. 1–4. The assembled device 10 is then used in sampling with a proximal end 124 of the cup 112 located next to the tether handle 34. After the foam 17 is saturated the fluid specimen, the foam 17 is removed from the mouth and, with one hand of a user holding the expresser cup 92, and another hand holding the handle 34, the foam is gently pulled into the cup 122, causing the foam 17 to enter the narrowing expresser cup 92 until a desired number of drops of the oral fluid is expressed therefrom. An open distal end 122 of the cup 112 may be placed over a collection area whereon the expressed fluid may be dropped for immediate testing or collection for later confirmation or use thereof. In this example, a slot such as 96, is preferably not provided. Assembly of the device 110 may be accomplished by threading the tether 24 through a proximal end opening 125, and subsequently attaching the absorbent member 17 to the tether 24 using suitable means.

In another aspect of the invention, individual drops of fluid may be obtained by carefully controlling manual pulling of the absorbent member into the expresser 120. As an example, a first drop of fluid may be obtained by pulling the absorbent member 17 into the expresser cup 112 and allowing the absorbent member 17 to be sufficiently compressed thereby to cause expression of only a single first drop of fluid. The first drop is thereafter collected onto a collection area. One or more additional drops of the fluid sample may be obtained by continuing to pull the absorbent member 17 further into the port and allowing the additional drops to flow and drop from the expresser cup 122. These additional drops may be deposited onto the same collection area or onto a different collection area (for example, into a standalone confirmation canister) by simply positioning the expresser 122 over the desired collection area. The above steps may be repeated until the desired number of drops are obtained and collected. The method may further comprise separately processing the drops of fluid. For example, the step of separately processing may comprise directing a first drop: onto a lateral flow test strip for testing, and storing a second drop in a canister or container for use in confirmation testing or otherwise processing at a later time.

It is to be appreciated that although the present devices 10, 120 were developed for use in the collecting and testing of oral fluid, for example saliva, with appropriate modification thereto, the devices 10, 120 may be adapted for the collection and testing of blood, plasma, serum, urine or other fluid specimens. For example, the absorbent member 17 may be made of materials presently known to those skilled in the art, to be suitable for the absorption of said other fluid specimens.

Although there has been hereinabove described a saliva sampling device, in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A fluid specimen sampling device comprising:
    an expresser having a distal opening and adapted to receive an absorbent member having a fluid absorbed therein;
    means, including a port of the expresser, for compressing the absorbent member as the absorbent member is passed into the expresser to effect expression of at least a portion of the fluid from the absorbent member; and
    collection means, connected to the expresser, for collecting the portion of fluid expressed from the absorbent member, said collection means comprising a platform including a sample well in fluid communication with the expresser distal opening.

2. The device according the claim 1 wherein the expresser is slanted with respect to the platform to facilitate a flow of the fluid expressed from the absorbent member and into the sample well.

3. The device according to claim 1 wherein the sample well includes a first port and a second port.

4. The device according to claim 3 wherein the first port and the second port comprise a test port and a confirmation port respectively.

5. The device according to claim 4 wherein the platform includes a lateral flow test strip in fluid communication with the test port, and a window for enabling viewing of at least a portion of the lateral flow test strip.

6. The device according to claim 4 wherein the collection means further includes a confirmation container depending from the platform and in fluid communication with the confirmation port.

7. The device according to claim 1 wherein the collection means comprises processing means, including a lateral flow test strip and a confirmation container, for respectively testing and confirming the portion of fluid expressed from the absorbent member.

8. The device according to claim 1 further comprising means for dividing the portion of fluid as the fluid is expressed and collected in the collection means.

9. The device according to claim 8 wherein the expresser is slanted with respect to the platform to facilitate a flow of the portion of fluid expressed from the absorbent member and into the sample well.

10. The device according to claim 8 wherein the sample well includes a first port and a second port.

11. The device according to claim 10 wherein the means for dividing comprises a partition extending substantially normal to the platform into the expresser distal opening and disposed between the first port and the second port.

12. The device according to claim 10 wherein the first port and the second port comprise a test port and a confirmation port respectively.

13. The device according to claim 12 wherein the platform includes a lateral flow test strip in fluid communication with the test port, and a window for enabling viewing of at least a portion of the lateral flow test strip.

14. The device according to claim 12 wherein the collection means further includes a confirmation container depending from the platform and in fluid communication with the confirmation port.

15. The device of claim 1 further comprising an absorbent member capable of absorbing a fluid specimen.

16. The device according to claim 15 wherein the absorbent member is capable of absorbing a saliva sample.

17. The device of claim 15 further comprising tether means, connected to the absorbent member, for controlling passage of the absorbent member into the expresser.

18. The device of claim 15 wherein the expresser further includes slot means for facilitating insertion of the absorbent member and tether means into the expresser.

19. The device of claim 18 further comprising means, including a narrow end of the slot means, for locking the tether means into the expresser and holding the absorbent member in a compressed position.

20. The device of claim 19 wherein the slot means includes an distal end inlet, sized for substantially uncompressed passage of the absorbent member, and a longitudinal slot in communication with the distal end inlet, sized for passage of the tether means.

21. The device according to claim 1 wherein the means for compressing further includes manually squeezable walls of the expresser.

22. The device according to claim 1 wherein the means for compressing further includes a conical shape of the expresser.

23. A saliva specimen sampling device comprising:
an absorbent member capable of absorbing a fluid specimen;
an expresser having a distal opening and adapted to receive the absorbent member;
means, including a port of the expresser, for comprising the absorbent member as the absorbent member is passed into the expresser to effect expression of at least a portion of the fluid specimen absorbed by the absorbent member; and
collection means, connected to the expresser for collecting the portion of the fluid specimen expressed from the absorbent member, said collection means comprising platform including a sample well in fluid communication with the expresser distal opening.

24. The device according to claim 23 wherein the absorbent member is capable of absorbing saliva fluid.

25. The device according to claim 23 wherein the expresser includes an aperture in a proximal end thereof, and the device further comprises tether means, passing through the aperture and connected to the absorbent member, for enabling manual pulling of the absorbent member into the expresser.

26. The device according to claim 23 further comprising means for dividing the portion of fluid expressed from the expresser and collected in the collection means.

27. The device according to claim 23 wherein the expresser is slanted with respect to the platform to facilitate a flow of the portion of fluid expressed from the absorbent member and into the sample well.

28. The device according to claim 23 wherein the sample well includes a first port and a second port.

29. The device according to claim 28 wherein the means for dividing comprises a partition extending substantially normal to the platform into the expresser distal opening and disposed between the first port arid the second port.

30. The device according to claim 28 wherein the first port and the second port comprise a test port and a confirmation port respectively.

31. A method of obtaining a desired number of drops of a saliva sample, the method comprising the steps of:
providing an absorbent member attached to a tether;
providing an expresser having an open distal end, a substantially closed proximal end, and an inner surface defining a port;
applying a fluid sample to the absorbent member and allowing the fluid sample to be absorbed thereby;
obtaining a first drop of the fluid sample from the absorbent member by pulling the absorbent member into the port by pulling the tether, and allowing the absorbent member to be compressed by the inner surface of the expresser to cause the first drop to be expressed from the absorbent member;
collecting the first drop of the fluid sample by allowing the first drop to flow from the expresser onto a collection area; and
obtaining and collecting additional drops of the fluid sample by continuing to pull the absorbent member further into the port and allowing the drops to flow onto the collection area until the desired number of drops are obtained and collected.

32. The method of claim 31 wherein the step of providing an expresser comprises providing an expresser having a substantially conical cross section.

33. The method according to claim 31 wherein the step of applying comprises placing the absorbent member in a mouth of a patient and allowing the absorbent member to absorb saliva from the mouth.

34. The method according to claim 31 further comprising separately processing the drops.

35. The method according to claim 34 wherein the step of separately processing comprises directing the first drop onto a lateral flow test strip for testing and storing, another drop in a container for processing of the second portion at a later time.

* * * * *